US011078431B2

(12) United States Patent
Koseoglu et al.

(10) Patent No.: US 11,078,431 B2
(45) Date of Patent: Aug. 3, 2021

(54) MODIFIED ULTRA-STABLE Y (USY) ZEOLITE CATALYST FOR DEOLEFINIZATION OF HYDROCARBON STREAMS

(71) Applicants: Saudi Arabian Oil Company, Dhahran (SA); JGC Catalysts and Chemicals Ltd., Kawasaki Kanagawa (JP); Japan Cooperation Center, Petroleum, Tokyo (JP)

(72) Inventors: Omer Refa Koseoglu, Dhahran (SA); Robert Peter Hodgkins, Dhahran (SA); Mitsunori Watabe, Kawasaki (JP); Tomoyasu Kagawa, Kawasaki (JP); Koji Uchida, Kawasaki (JP)

(73) Assignees: Saudi Arabian Oil Company, Dhahran (SA); JGC CATALYSTS AND CHEMICALS LTD., Kawasaki Kanagawa (JP); JAPAN COOPERATION CENTER, PETROLEUM, Tokyo (JP)

( * ) Notice: Subject to any disclaimer, the term of this patent is extended or adjusted under 35 U.S.C. 154(b) by 0 days.

(21) Appl. No.: 16/715,555

(22) Filed: Dec. 16, 2019

(65) Prior Publication Data

US 2021/0179949 A1 Jun. 17, 2021

(51) Int. Cl.
*C10G 35/06* (2006.01)
*B01J 29/08* (2006.01)
*C10G 35/24* (2006.01)

(52) U.S. Cl.
CPC .......... *C10G 35/065* (2013.01); *B01J 29/088* (2013.01); *C10G 35/24* (2013.01); *B01J 2229/183* (2013.01); *C10G 2300/1096* (2013.01); *C10G 2300/4006* (2013.01);
(Continued)

(58) Field of Classification Search
CPC .............. C10G 35/065; C10G 35/24; C10G 2300/1096; C10G 2300/4006; C10G 2300/4012; C10G 2300/4018; C10G 2400/30; B01J 29/088; B01J 2229/183
See application file for complete search history.

(56) References Cited

U.S. PATENT DOCUMENTS

| 4,191,635 A | 3/1980 | Quick et al. |
| 4,918,225 A | 4/1990 | Rittner et al. |
| 5,310,477 A | 5/1994 | Lomas |

(Continued)

FOREIGN PATENT DOCUMENTS

| JP | 6001531 B2 | 10/2016 |
| JP | 6042328 B2 | 12/2016 |

OTHER PUBLICATIONS

Juarez, Raquel, et al. "Transition metal containing zeolites and mesoporous MCM-41 as heterogeneous catalysts for the N-alkylation of 2, 4-diaminotoluene with dimethylcarbonate." Catalysis Communications 10.5 (2009): 472-476.

(Continued)

*Primary Examiner* — Brian A McCaig
(74) *Attorney, Agent, or Firm* — Leason Ellis LLP

(57) ABSTRACT

The present disclosure relates to a process for the deolefinization of hydrocarbon streams through an aromatic alkylation reaction by olefins, using a catalyst containing a framework-substituted zirconium and/or titanium and/or hafnium-modified ultra-stable Y (USY) type zeolite.

28 Claims, 6 Drawing Sheets

(52) U.S. Cl.
CPC ............... *C10G 2300/4012* (2013.01); *C10G 2300/4018* (2013.01); *C10G 2400/30* (2013.01)

(56) References Cited

U.S. PATENT DOCUMENTS

| | | | |
|---|---|---|---|
| 6,103,948 | A | 8/2000 | Ginosar et al. |
| 6,855,856 | B2 | 2/2005 | Van Broekhoven et al. |
| 6,884,339 | B2 | 4/2005 | Benazzi et al. |
| 7,550,405 | B2 | 6/2009 | Shan et al. |
| 7,592,282 | B2 | 9/2009 | Ginosar et al. |
| 7,750,197 | B2 | 7/2010 | Van Broekhoven et al. |
| 7,858,069 | B2 | 12/2010 | Ginosar et al. |
| 8,163,969 | B2 | 4/2012 | Van Broekhoven et al. |
| 8,395,006 | B2 | 3/2013 | Clark et al. |
| 8,574,542 | B2 | 11/2013 | Domokos et al. |
| 8,937,205 | B2 | 1/2015 | Iaccino et al. |
| 9,012,696 | B2 | 4/2015 | Calaresu et al. |
| 9,145,522 | B2 | 9/2015 | Negiz et al. |
| 9,150,494 | B2 | 10/2015 | Tonkovich et al. |
| 9,238,599 | B2 | 1/2016 | Winsett |
| 9,376,325 | B2 | 6/2016 | Domokos et al. |
| 10,071,939 | B2 | 9/2018 | Abudawoud |
| 10,173,950 | B2 | 1/2019 | Abudawoud et al. |
| 10,427,143 | B2 | 1/2019 | Domokos et al. |
| 10,293,332 | B2 | 5/2019 | Koseoglu et al. |
| 2003/0168379 | A1 | 9/2003 | Degnan et al. |
| 2004/0162454 | A1 | 8/2004 | Gao et al. |
| 2006/0020154 | A1 | 1/2006 | Lo et al. |
| 2010/0305373 | A1 | 2/2010 | Bema et al. |
| 2013/0175202 | A1 | 7/2013 | Koseoglu et al. |
| 2014/0190868 | A1* | 7/2014 | Koseoglu ............... B01J 29/084 208/58 |
| 2014/0262956 | A1 | 9/2014 | Duma et al. |
| 2019/0194095 | A1 | 6/2019 | Xu et al. |

OTHER PUBLICATIONS

International Search Report and Written Opinion in Corresponding PCT Application No. PCT/US2020/064836 dated Mar. 19, 2021. 9 pages.

\* cited by examiner

MODIFIED ULTRA-STABLE Y (USY) ZEOLITE CATALYST FOR DEOLEFINIZATION OF HYDROCARBON STREAMS

FIELD OF THE INVENTION

The present disclosure relates to a process for the deolefinization of hydrocarbon streams through an aromatic alkylation reaction by olefins, using catalysts containing a framework-substituted zirconium and/or titanium and/or hafnium-modified ultra-stable Y (USY) type zeolite.

BACKGROUND OF THE INVENTION

Refinery products used for fuels are receiving increasing levels of attention. Product specifications are being scrutinized by governmental agencies whose interests are decreased emissions from mobile and stationary sources, and by the industries that produce the engines and vehicles that utilize these fuels. Regional and national regulations have been in place and continue to evolve concerning gasoline specifications, and automakers have proposed a set of limitations for gasoline and diesel to allow them to manufacture vehicles which will produce significantly lower emissions over their lifetime. Maximum sulfur, aromatics, and benzene levels of 10 ppmw, 25 V %, and 1 V % or less, respectively, have been targeted as goals by regulators.

Historically, lead was commonly added to gasoline to increase octane. When the use of lead was phased out due to environmental concerns, no direct substitute existed, and refiners instead have converted certain hydrocarbon molecules used in gasoline blending in order to achieve higher octane ratings. Catalytic reforming, which involves a variety of reactions in the presence of one or more catalysts in the presence of recycle and make-up hydrogen, is a widely used process for refining hydrocarbon mixtures to increase the yield of higher octane gasoline.

In a typical refinery, naphtha is reformed after hydrodesulfurization to increase the octane number of the gasoline. The reformate contains a high level of benzene which must be reduced in order to meet requisite fuel specifications that are commonly in the range of from about 1-3 V % benzene, with certain geographic regions targeting a benzene content of less than 1 V %. Existing methods to remove benzene from reformate include separation processes and hydrogenation processes. In separation processes, benzene is typically extracted with a solvent and then separated from the solvent in a membrane separation unit or other suitable unit operation. In hydrogenation processes, a naphtha stream is first hydrotreated in hydrotreating unit to produce a hydrotreated naphtha stream. The hydrotreating unit operates under conditions effective to remove at least enough sulfur and nitrogen to meet requisite product specifications. For instance, hydrotreating in conventional naphtha reforming systems generally occurs under relatively mild conditions that are effective to remove sulfur and nitrogen to less than 0.5 ppmw levels. The hydrotreated naphtha stream is reformed in reforming unit to produce a gasoline reformate product stream. The reformate is sent to the gasoline pool to be blended with other gasoline components to meet the specifications. A typical gasoline blending pool includes C4 and heavier hydrocarbons having boiling points of less than about 205° C.

In the catalytic reforming process, paraffins and naphthenes are restructured to produce isomerized paraffins and aromatics of relatively higher octane numbers. The catalytic reforming converts low octane n-paraffins to i-paraffins and naphthenes. Naphthenes are converted to higher octane aromatics. The aromatics are left essentially unchanged or some may be hydrogenated to form naphthenes due to reverse reactions taking place in the presence of hydrogen.

The reactions involved in catalytic reforming are commonly grouped into the four categories of cracking, dehydrocyclization, dehydrogenation and isomerization. A particular hydrocarbon/naphtha feed molecule may undergo more than one category of reaction and/or may form more than one product. The catalysts for catalytic reforming processes are either mono-functional or bi-functional reforming catalyst which contains precious metals, i.e., IUPAC Groups 8-10 metals, as active components. A bi-functional catalyst has both metal sites and acidic sites. Refineries generally use a platinum catalyst and/or palladium supported on alumina as the reforming catalyst.

The reformate is usually sent to an aromatics recovery complex where it undergoes several processing steps in order to recover high value products, e.g., xylenes and benzene, and to convert lower value products, e.g., toluene, into higher value products. For example, the aromatics present in the reformate are usually separated into different fractions by carbon number; e.g. benzene, toluene, xylenes, and ethylbenzene, etc. The C8 fraction is then subjected to a processing scheme to make more high value para-xylene. Para-xylene is usually recovered in high purity from the C8 fraction by separating the para-xylene from the ortho-xylene, meta-xylene, and ethylbenzene using selective adsorption or crystallization. The ortho-xylene and meta-xylene remaining from the para-xylene separation are isomerized to produce an equilibrium mixture of xylenes. The ethylbenzene is isomerized into xylenes or is dealkylated to benzene and ethane. The para-xylene is then separated from the ortho-xylene and the meta-xylene using adsorption or crystallization and the para-xylene-deleted-stream is recycled to extinction to the isomerization unit and then to the para-xylene recovery unit until all of the ortho-xylene and meta-xylene are converted to para-xylene and recovered.

In an aromatics complex, a variety of process units are used to convert naphtha or pyrolysis gasoline into benzene, toluene and mixed xylenes ("BTX"), which are basic petrochemical intermediates used for the production of various other chemical products. In order to maximize the production of BTX the feed to an aromatics complex is generally limited from C6 up to C11 compounds. In most aromatic complexes, the mixed xylenes are processed within the complex to produce the particular isomer-para-xylene, which can be processed downstream to produce terephthalic acid. This terephthalic acid is used to make polyesters, such as polyethylene terephthalate. In order to increase the production of benzene and para-xylene, the toluene and C9 and C10 aromatics are processed within the complex through a toluene, C9, C10 transalkylation/toluene disproportionation (TA/TDP) process unit to produce benzene and xylenes. Any remaining toluene, C9, and C10 aromatics are recycled to extinction. Compounds heavier than C10 are generally not processed in the TA/TDP unit, as they tend to cause rapid deactivation of the catalysts used at the higher temperatures used in these units, often greater than 400° C.

When para-xylene is recovered from mixed xylenes by a selective adsorption process unit in the complex, the C8 feed to the selective adsorption unit is processed to eliminate olefins and alkenyl aromatics such as styrene in the feed. Olefinic material can react and occlude the pores of the zeolite adsorbent. There are two known methods to remove olefins: (1) selective hydrogenation; and (2) clay treatment.

According to existing methods, the olefinic material is removed by passing a C8+ stream across a clay or acidic catalyst to react olefins and alkenyl aromatics with another (typically aromatic) molecule, forming heavier compounds (C16+).

These heavier compounds are typically removed from the mixed xylenes by fractionation. The heavy compounds cannot be processed in the TA/TDP unit due to their tendency to deactivate the catalyst and are generally removed from the complex as lower value fuels blend stock.

Clay treating is used to reduce olefins content and thus, lower the Bromine Index (BI) of heavy reformate and aromatic extract streams in an aromatic recovery complex. In the process, a stream of either mixed xylenes, benzene/toluene or a combination of each is preheated in a feed heater. The stream is then sent to a liquid-phase reactor containing the clay catalyst. The reactor consists of two vessels with one in service and one in standby mode. The primary reaction is the acid-catalyzed alkylation of an aromatic molecule with an olefin, resulting in the formation of a heavy aromatic compound. The heavy aromatic compound is then fractionated and obtained as a process bottoms stream.

However, clay treatment has disadvantages such as cycle length which is about 6 months so the clay must be changed, and formation of a heavier stream. There is a need in the art to find an alternative catalyst for deolefinization reactions.

SUMMARY

The present disclosure provides a process to deolefinate (i.e., remove olefins from) hydrocarbon streams through an aromatic alkylation reaction by olefins, using a catalyst containing zirconium and/or titanium and/or hafnium-modified ultra-stable Y (USY) type zeolite.

The present disclosure provides an alternative catalyst and process for deolefinization of aromatic-rich reformate by replacing the clay used in conventional processes with a catalyst containing post-modified, frame-work substituted ultra-stable Y (USY) zeolite in which titanium (Ti), zirconium (Zr) and/or hafnium (Hf) are inserted into the zeolite catalyst after dealumination. The process utilizes the framework-substituted USY zeolite catalyst to deolefinate aromatic-rich hydrocarbon streams by aromatic alkylation reactions using olefins as the alkylation agents. As demonstrated herein, an FCC naphtha sample used as feedstock was treated with a modified USY zeolite containing catalyst according to the present disclosure. GC-MS comparison of the m/z 190 ion (representing all C7 aromatic compounds) between the initial FCC naphtha feed and a sample treated with a modified USY zeolite catalyst shows emerging new, higher molecular weight products representing aromatic alkylated products. FT-MS analysis confirms that FCC naphtha alkylation took place by adding approximately 4-8 carbon atoms on average, while retaining similar double bond equivalence.

Thus, in some embodiments, the present disclosure provides a process for deolefinization of a hydrocarbon feed containing aromatic compounds and olefins, by contacting the hydrocarbon feed with a catalyst containing a framework-substituted ultra-stable Y (USY)-type zeolite.

In other embodiments, the present disclosure provides a process for alkylating aromatic compounds in a hydrocarbon feed containing aromatic compounds and olefins, by contacting the hydrocarbon feed with a catalyst containing a framework-substituted ultra-stable Y (USY)-type zeolite.

In the process of the present disclosure, the olefins function as alkylating agents of aromatics present in the hydrocarbon feed, thereby producing alkylated aromatic compounds and a deolefinated hydrocarbon product.

In some embodiments, a catalyst containing a framework-substituted ultra-stable Y (USY)-type zeolite is one wherein a portion of aluminum atoms constituting a zeolite framework thereof is substituted with zirconium atoms and/or titanium and/or hafnium atoms.

In some embodiments, the framework-modified USY zeolite may be carried on a support which contains an inorganic oxide, e.g., alumina, silica-alumina and the like, as described herein.

Further embodiments and the full scope of applicability of the present disclosure will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

A more complete understanding of the invention and its many features and advantages will be attained by reference to the following detailed description and the accompanying drawing. It is important to note that the drawing illustrates only one embodiment of the present disclosure and therefore should not be considered to limit its scope.

DETAILED DESCRIPTION OF CERTAIN EMBODIMENTS

Figure 1A:
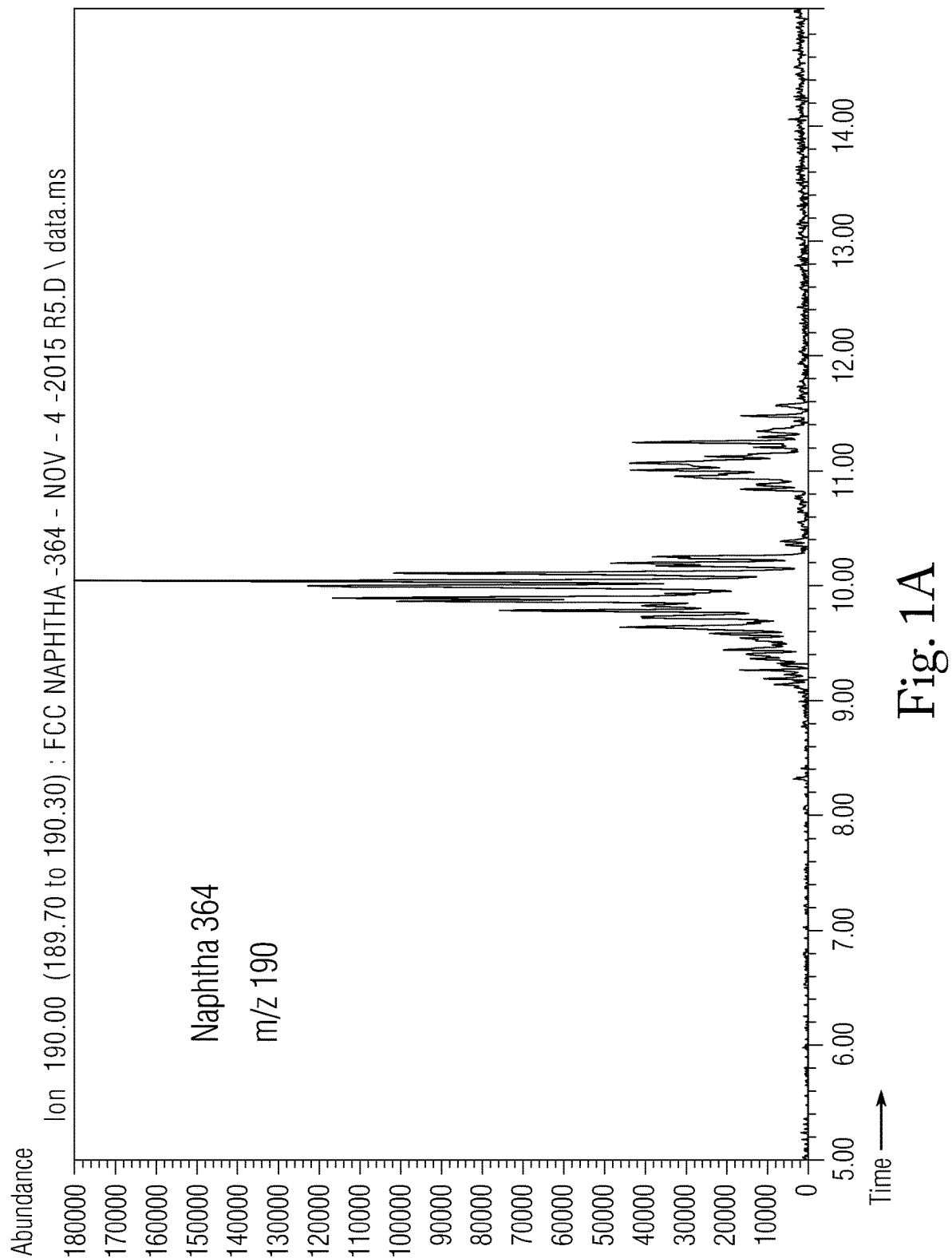
FIGS. 1A-1B depicts GC-MS comparisons of the m/z 190 ion of a FCC naphtha feed (FIG. 1A, Naphtha 364) and reaction product RPHSA-5 (FIG. 1B).

The present disclosure relates to a process for deolefinization of a hydrocarbon feed containing aromatic compounds and olefins, the process comprising the step of contacting the hydrocarbon feed with a catalyst containing a framework-substituted ultra-stable Y (USY)-type zeolite in which a portion of aluminum atoms constituting a zeolite framework thereof is substituted with zirconium atoms and/or titanium and/or hafnium atoms, wherein the olefins alkylate the aromatic compounds in the hydrocarbon feed, thereby producing a deolefinated hydrocarbon product.

The present disclosure further relates to a process alkylating aromatic compounds in a hydrocarbon feed containing aromatic compounds and olefins, the process comprising the step of contacting the hydrocarbon feed with a catalyst containing a framework-substituted ultra-stable Y (USY)-type zeolite in which a portion of aluminum atoms constituting a zeolite framework thereof is substituted with zirconium atoms and/or titanium atoms and/or hafnium atoms, wherein the olefins alkylate the aromatic compounds in the hydrocarbon feed, thereby producing alkylated aromatic compounds.

Catalyst with Framework Substituted Ultra Stable Y (USY) Zeolite

The catalyst used in the process of the present invention contains a framework substituted zeolite in which a part of aluminum atoms constituting a zeolite framework is substituted with zirconium atoms and/or titanium atoms and/or hafnium atoms.

In some embodiments, the catalyst with the framework-substituted zeolite catalyst used in the process of the present disclosure is an ultra-stable Y-type zeolite in which silicon atoms and aluminum atoms form a zeolite framework and in which a part of the aluminum atoms is substituted with zirconium atoms and/or titanium atoms and/or hafnium atoms. For example, the framework-substituted zeolite in the catalyst in which a part of aluminum atoms forming a zeolite framework is substituted only with zirconium atoms is referred to as a "zirconium-substituted zeolite" or "Zr-USY"; the framework-substituted zeolite in the catalyst in which a part of aluminum atoms forming a zeolite framework of the framework-substituted zeolite is substituted only with titanium atoms is referred to as a "titanium-substituted zeolite" or "Ti-USY"; the framework-substituted zeolite in the catalyst in which a part of aluminum atoms forming a zeolite framework is substituted only with zirconium atoms and titanium atoms is referred to as a "zirconium.titanium-substituted zeolite" or "Zr.Ti-USY"); and the framework-substituted zeolite in the catalyst in which a part of aluminum atoms forming a zeolite framework is with zirconium atoms, titanium and hafnium atoms is referred to as "zirconium.titanium.hafnium substituted zeolite" or "Zr.Ti.Hf-USY".

Zirconium atoms and/or titanium and/or hafnium atoms which are substituted for the aluminum atoms forming a framework of the ultra-stable Y-type zeolite serve as constituents of the framework of the ultra-stable Y-type zeolite. Substitution can be verified by, e.g., ultraviolet, visible, and near-infrared spectrophotometry (UV-Vis-NIR), Fourier transform infrared spectroscopy (FT-IR), or nuclear magnetic resonance spectrometry (NMR).

In some embodiments, in addition to the substituted atoms, the zirconium atoms and/or titanium and/or hafnium atoms may further be attached (carried) to the outside of, or combined with the framework of the USY-type catalyst, as described in U.S. Pat. No. 10,293,332, which is hereby incorporated by reference in its entirety as if fully set forth herein.

In some embodiment, the framework-substituted zeolite of the catalyst contains about 0.1% to about 5%, preferably about 0.2% to about 4%, more preferably about 0.3% to about 3% zirconium atoms and/or titanium and/or hafnium atoms by mass in terms of oxide (i.e., "$ZrO_2$", "$TiO_2$" and "$HfO_2$") based on the framework-substituted zeolite. As contemplated herein, a content range (based on oxides) of zirconium atoms and/or titanium atoms and/or hafnium atoms includes all of the contents of zirconium atoms and/or titanium and/or hafnium atoms substituted for aluminum atoms forming a zeolite framework and zirconium atoms and/or titanium and/or hafnium atoms which are not substituted for the above aluminum atoms.

It is appreciated by a person of skill in the art, that when the framework-substituted zeolite in the catalyst contains the zirconium atoms and the titanium atoms and/or the hafnium atoms described above, a mass ratio (in terms of oxides) of the zirconium atoms to the titanium atoms and/or the hafnium atoms is not specifically be restricted, and any ratio of zirconium or titanium or hafnium that is effective to carry out the process of the present invention may be used.

The zirconium atom and/or titanium and/or hafnium atom content of the framework-substituted zeolite in the catalyst can be measured with, for example, an X-ray fluorescence analyzer, a high frequency plasma emission spectrometer, an atomic absorption spectrometer or the like.

In some embodiments, particles of the zirconium and/or titanium and/or hafnium-modified USY catalyst have a diameter of 50 nm or less.

Method for Producing the Framework-Substituted Zeolite

The framework-substituted zeolite in the catalyst in the present invention can be produced in accordance with the methods described by U.S. Pat. No. 10,293,332. For example, the framework-substituted zeolite in the catalyst may be produced by firing a USY-type zeolite at 500° C. to 700° C., the USY-type zeolite having a crystal lattice constant of 2.430 to 2.450 nm, a specific surface area of 600 to 900 $m^2/g$, and a molar ratio of $SiO_2$ to $Al_2O_3$ of 20 to 100, forming a suspension containing the fired USY-type zeolite, the suspension having a liquid/solid mass ratio of 5 to 15, adding an inorganic acid or an organic acid so that a pH of the above suspension is 1.0 to 2.0, subsequently adding a solution containing a zirconium compound and/or a hafnium compound and mixing them and neutralizing the solution with, for example, an aqueous ammonia in such a manner that the mixed solution has a pH of about 7.

Ultra-stable Y-type zeolite is used as one of the raw materials for preparing the framework-substituted zeolite in the catalyst. Ultra-stable Y-type zeolite means zeolite having a crystal lattice constant (UD) falling in a range of 2.430 nm or more and 2.450 nm or less, a specific surface area of 600 to 900 $m^2/g$ and a molar ratio (silica-alumina ratio) falling in a range of 20 to 100 in terms of $SiO_2$ to $Al_2O_3$. The ultra-stable Y-type zeolite may be prepared by any method known in the art.

In the method for producing the framework-modified ultra-stable Y-type zeolite, extraskeletal aluminum (aluminum atoms which do not form the zeolite framework) may be removed from the ultra-stable Y-type zeolite raw material in order to obtain the ultra-stable Y-type zeolite. Extraskeletal aluminum can be removed by, for example, a method of dispersing the ultra-stable Y-type zeolite in warm water of 40 to 95° C. to prepare a suspension, adding sulfuric acid to the above suspension and stirring it for 10 minutes to 3 hours while maintaining the temperature at 40 to 95° C. to thereby dissolve the extraskeletal aluminum. After dissolving the extraskeletal aluminum, the suspension is filtrated, and a residue on the filter is washed with purified water of 40 to 95° C. and dried at 100 to 180° C. for 3 to 30 hours, whereby an ultra-stable Y-type zeolite from which the extraskeletal aluminum is removed can be obtained.

Furthermore, in the method for producing the framework-modified ultra-stable Y-type zeolite, the ultra-stable Y-type zeolite raw material may be calcined at 500° C. to 700° C., preferably 550° C. to 650° C. The calcining time shall not specifically be restricted as long as the targeted framework-substituted zeolite is obtained, and it is calcined in a range of, for example, 30 minutes to 10 hours. In respect to a calcining atmosphere of the ultra-stable Y-type zeolite, it is carried out preferably in the air. The calcined ultra-stable Y-type zeolite is suspended in water having a temperature of about 20° C. to about 30° C. to form a suspension. With respect to the concentration of the suspension of the ultra-stable Y-type zeolite, the liquid/solid mass ratio is preferably in the range of 5 to 15, and more preferably, a mass ratio of 8 to 12 is recommended.

Next, an inorganic acid or an organic acid is added thereto so that a pH of the suspension described above is controlled to 1.0 to 2.0, and subsequently a solution containing a zirconium compound and/or a hafnium compound is added and mixed. Then, the mixed solution is neutralized (pH 7.0 to 7.5) and dried desirably at 80 to 180° C., whereby the framework-substituted zeolite described above can be obtained.

Sulfuric acid, nitric acid, hydrochloric acid and the like can be given as the above inorganic acid used, and among them, sulfuric acid, hydrochloric acid and the like are particularly preferred. Further, carboxylic acids can suitably be used as the organic acid described above. A use amount of the inorganic acid or the organic acid shall not be restricted as long as a pH of the suspension can be controlled to a range of 1.0 to 2.0, and it is, for example, a 0.5- to 4.0-fold molar amount and preferably 0.7- to 3.5-fold molar amount based on an amount of $Al_2O_3$ in the ultra-stable Y-type zeolite, but it shall not be restricted to the above range.

Examples of the zirconium compound described above include zirconium sulfate, zirconium nitrate, zirconium chloride and the like. Among these compounds, zirconium sulfate, zirconium nitrate, and the like are particularly preferred. The amount of the zirconium compound added is preferably about 0.1% to about 5% by mass and more preferably about 0.2% to about 4% by mass on a zirconium oxide basis with respect to the ultra-stable Y-type zeolite described above. Usually, an aqueous solution of a zirconium compound prepared by dissolving the zirconium compound in water is suitably used as the zirconium compound.

Examples of the hafnium compound described above include hafnium chloride, hafnium nitrate, hafnium fluoride, hafnium bromide, hafnium oxalate and the like. Among these compounds, hafnium chloride, hafnium nitrate, and the like are particularly preferred. The amount of the hafnium compound added is preferably about 0.1% to about 5% by mass and more preferably about 0.2% to about 4% by mass on a hafnium oxide basis with respect to the ultra-stable Y-type zeolite. Usually, an aqueous solution of a hafnium compound prepared by dissolving the hafnium compound in water is suitably used as the hafnium compound.

In some embodiments, a titanium compound may be added to the mixed solution described above. Examples of the titanium compound include titanium sulfate, titanium acetate, titanium chloride, titanium nitrate, and titanium lactate. Among these compounds, titanium sulfate, titanium acetate, and the like are particularly preferred. The amount of the titanium compound added is preferably about 0.1% to about 5% by mass and more preferably about 0.2% to about 4% by mass on an oxide basis with respect to the ultra-stable Y-type zeolite. Usually, an aqueous solution of a titanium compound prepared by dissolving the titanium compound in water is suitably used as the titanium compound.

A pH of the above suspension has to be controlled in advance to 1.0 to 2.0 for the purpose of preventing precipitation from being generated in mixing an aqueous solution of the zirconium compound, the hafnium compound or the titanium compound with a suspension of the ultra-stable Y-type zeolite described above.

In the case of mixing an aqueous solution of the zirconium compound, the hafnium compound or the titanium compound with a suspension of the ultra-stable Y-type zeolite, preferably, the above aqueous solution is gradually added to the suspension. After finishing addition of the aqueous solution described above to the suspension, the solution is preferably mixed by stirring at, for example, room temperature (about 25° C. to about 35° C.) for 3 to 5 hours. Further, after finishing the mixing described above, the mixed solution described above is neutralized by adding an alkali such as aqueous ammonia and the like so that a pH thereof is controlled to 7.0 to 7.5, whereby the framework-substituted zeolite in the catalyst can be obtained.

It is apparent to a person of skill in the art, that when only the zirconium compound (or an aqueous solution thereof) is used as the compound (or an aqueous solution thereof) added to the suspension described above, the framework-substituted zeolite in the catalyst (Zr-USY) in which zirconium atoms is substituted for a part of aluminum atoms forming the framework of the ultra-stable Y-type zeolite is formed; when only the hafnium compound (or an aqueous solution thereof) is used, the framework-substituted zeolite in the catalyst (Hf-USY) in which hafnium atoms is substituted for a part of aluminum atoms forming the framework of the ultra-stable Y-type zeolite is formed; when only the titanium compound (or an aqueous solution thereof) is used, the framework-substituted zeolite in the catalyst (Ti-USY) in which titanium atoms is substituted for a part of aluminum atoms forming the framework of the ultra-stable Y-type zeolite is formed; when the zirconium compound and the titanium compound (or aqueous solutions thereof) are used, the framework-substituted zeolite in the catalyst (Zr.Ti-USY) in which zirconium atoms and titanium atoms are substituted for a part of aluminum atoms forming the framework of the ultra-stable Y-type zeolite is formed; when the zirconium compound and the hafnium compound (or aqueous solutions thereof) are used, the framework-substituted zeolite in the catalyst (Zr.Hf-USY) in which zirconium atoms and hafnium atoms are substituted for a part of aluminum atoms forming the framework of the ultra-stable Y-type zeolite is formed; and when the zirconium compound, the titanium compound and the hafnium compound (or aqueous solutions thereof) are used, the framework-substituted zeolite in the catalyst (Zr.Ti.Hf-USY) in which zirconium atoms, titanium atoms and hafnium atoms are substituted for a part of aluminum atoms forming the framework of the ultra-stable Y-type zeolite is formed.

The resulting framework-substituted zeolite in the catalyst is preferably filtered, if desired, washed with water, and dried at about 80° C. to about 180° C.

The framework-modified USY zeolite may be carried on a support which contains an inorganic oxide excluding the above framework-substituted zeolite in the catalyst in addition to the framework-substituted zeolite in the catalyst described above. The inorganic oxide typically contains a substance serving as a granulating agent or a binder. Usually, a known substance that is contained in a support including the ultra-stable Y-type zeolite and that is used as a granulating agent or the like can be used. Examples of inorganic oxides include, but are not limited to alumina, silica, titania, silica-alumina, alumina-titania, alumina-zirconia, alumina-boria, phosphorus-alumina, silica-alumina-boria, phosphorus-alumina-boria, phosphorus-alumina-silica, silica-alumina-titania, and silica-alumina-zirconia. In the present disclosure, in particular, an inorganic oxide mainly composed of alumina, silica-alumina is preferred.

The content of the framework-substituted zeolite in the catalyst and the inorganic oxide content of the support can be appropriately determined according to the object. The support includes a framework-substituted zeolite in the catalyst of about 2% to about 80% by mass, preferably about 10% to about 80% by mass, and more preferably about 20% to about 70% by mass, and an inorganic oxide content of about 98% to about 20% by mass, preferably about 90% to about 20% by mass and more preferably about 80% to about 30% by mass.

Metal Component:

The catalyst used in the process of the present disclosure may further include active metal components selected from the group consisting of IUPAC Group 7 to 11 metals of the Periodic Table. Examples of active metals include iron, cobalt, nickel, rhodium, palladium, silver, iridium, platinum or gold in group 8 of the long periodic table and/or metal components chromium, molybdenum or tungsten in group 6. Preferred examples of the metal component include combinations of molybdenum or tungsten in group 6 and cobalt or nickel in group 8; and metal components of the platinum group (platinum, rhodium, palladium and the like).

The metal component may be contained in the catalyst in an amount of about 0.01 to about 40% by mass in terms of oxide. In the case of molybdenum, tungsten, cobalt or nickel, an amount thereof is particularly preferably about 3 to about 30% by mass in terms of oxide based on a mass of the catalyst. In the case of the platinum group (platinum, rhodium, palladium and the like), an amount thereof is particularly preferably about 0.01 to about 2% by mass in terms of metal.

Apparatus/Process Parameters for Aromatic Alkylation/Deolefinization

An apparatus for the aromatic alkylation and deolefinization process in the present disclosure is not particularly limited as long as the foregoing reactions are carried out. Various types of apparatuses may be used. In accordance with some embodiments, the process of the present disclosure may be conducted in a fixed-bed reactor, on ebullated-bed or slurry-bed or moving-bed reactors or CSTR or batch type reactors, and the like.

Hydrocarbon Feed

The hydrocarbon feed used in the process of the invention may be any hydrocarbon feed that is rich in aromatic hydrocarbons. In some embodiments, the aromatic hydrocarbon feed is a reformate formed by a catalytic reforming process. Suitable reformates include, but are not limited to, light cut reformates, heavy reformates or heart cut reformates. The hydrocarbon feed is preferably enriched in aromatic hydrocarbons, such as C6-C8 aromatics. In one preferred embodiment, the aromatic-rich hydrocarbon feed is fluid catalytic cracking (FCC) naphtha. In other embodiments, the aromatic-rich hydrocarbon feed is any one or more of coking naphtha or other naphtha coming from the cracking units in which no hydrogen is used.

Reformate feeds usually contain very low amount of sulfur, as they are typically subjected to desulfurization prior to reforming such that the resulting gasoline product contains an acceptable level of sulfur for compliance with current sulfur specification. Aromatic streams from other sources, e.g., FCC naphtha, generally contain higher levels of impurities than reformate and therefore typically require feed pretreatment to remove contaminants, especially nitrogen (N) and sulfur (S) species. Removal of these species can be effectuated by conventional treatments such as fractionation, adsorption and/or hydrotreating/stripping. In some embodiments, the deolefinated hydrocarbon product preferably contains less than about 500 ppm sulfur, preferably less than about 10 ppm, most preferably less than about 0.5 ppm. In other embodiments, the deolefinated hydrocarbon product containing less than about 100 ppm nitrogen, preferably less than about 10 ppm, most preferably less than about 0.5 ppm.

In some embodiments, the hydrocarbon feed comprises an aromatic rich hydrocarbon oil having a boiling point range of about 15° C. to about 500° C. In other embodiments, the hydrocarbon feed comprises an aromatic rich hydrocarbon oil having a boiling point range of about 15° C. to about 250° C. In other embodiments, the hydrocarbon feed comprises an aromatic rich hydrocarbon oil having a boiling point range of about 250° C. to about 500° C. In other embodiments, the hydrocarbon feed comprises an aromatic rich hydrocarbon oil having a boiling point range of about 250° C. to about 400° C.

In some embodiments, the aromatic rich hydrocarbon stream has a bromine index at least less than 60,000, preferably less than 10,000, most preferably less than 1,000. As used herein, the term "bromine index" (BI) indicates olefinicity of a hydrocarbon sample and determined by a potentiometric titration. According to the reaction, one mole of olefin molecule consumes 1 mole of bromine so the test is report as mg of bromine per 100 g of hydrocarbon sample, which is bromine number. Bromine index is 1000 times of the bromine number. The reaction is

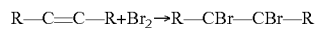

wherein each "R" is part of the olefin chain.

As detailed herein, in the process of the present disclosure, olefins present in the aromatic-rich hydrocarbon function as alkylating agents to alkylate the aromatic fraction, resulting in a product having a higher molecular weight aromatic fraction as compared with the initial aromatic fee. In some embodiments, the alkylation reaction adds approximately 2 to 10 carbon atoms on average. In other embodiments, the alkylation reaction adds approximately 4 to 10 carbon atoms on average. In other embodiments, the alkylation reaction adds approximately 4 to 8 carbon atoms on average. In some embodiments, the aromatic compounds in the hydrocarbon feed are selected from the group consisting of benzene, toluene, o-xylene, m-xylene, p-xylene, ethylbenzene, and combinations thereof, while the alkylated aromatic compounds are selected from the group consisting of toluene, o-xylene, m-xylene, p-xylene, ethylbenzene, or higher aromatic fraction containing C9+ aromatics.

As used herein, the term "BTX" means a composition comprising benzene (C6), toluene (C7) and mixed xylenes (C8). The term "xylenes" as denoted herein means any one of ortho xylene (o-xylene), meta-xylene (m-xylene), para-xylene (p-xylene) or any combination thereof. As used throughout, "mixed xylenes" refers to any one or more of o-xylene, m-xylene and p-xylene.

As used throughout, a reference to "C" and a number refers to the number of carbon atoms in a hydrocarbon. For example, C6 refers to a hydrocarbon with 6 carbon atoms, and C7 refers to a hydrocarbon with seven carbon atoms, and the like.

As a result of the alkylation reaction, the amount of olefins in the hydrocarbon product is reduced relative to the amount of olefins in the initial feed. Thus, in some embodiments, the deolefinated hydrocarbon product comprises less olefin hydrocarbons and more alkylated aromatic compounds compared with the hydrocarbon feed.

In some non-limiting embodiments, the hydrocarbon feed contains greater than about 1 wt % olefins. In other embodiments, the hydrocarbon feed contains greater than about 10 wt % olefins. In other embodiments, the hydrocarbon feed contains greater than about 25 wt % olefins. In other embodiments, the deolefinated hydrocarbon product contains less than about 10 wt % olefins, preferably less than about 1 wt % olefins, more preferably less than about 0.5 wt % olefins. In still other embodiments, the hydrocarbon feed stream is deolefinated at least about 95 wt %, preferably at least about 99 wt %, more preferably at least about 99.99 wt %.

As used herein, the term "olefin" denotes a compound with one or more carbon-carbon double bond. Non-limiting examples of olefins includes light olefins such as ethylene, propylene, butenes, or longer chain olefins, e.g., pentenes, hexenes pentenes, octenes and the like.

The process is conducted at conditions suitable for effectuating an aromatic alkylation/deolefinization reaction. A person of skill in the art can determine process parameter such as temperature and pressure to achieve the desired result. In some embodiments, the process is operated at a reaction temperature range of about 50° C. to about 250° C., a pressure of about 1 to about 30 bars and a liquid hourly space velocity (LHSV) of about 0.5 to about 5 $h^{-1}$.

EXAMPLES

The following examples are provided to better illustrate embodiments of the present disclosure. However, it is to be understood that these examples are merely illustrative in nature, and that the process embodiments of the present disclosure are not necessarily limited thereto.

Example 1: Materials and Methods

An FCC naphtha sample, the properties and composition of which are shown in Table 1, was used as a feedstock to demonstrate aromatic alkylation. The experiments were conducted in a round bottom flask with a condenser. The solid catalyst was added to the liquid and refluxed.

TABLE 1

| Feedstock properties | | |
|---|---|---|
| Property/Composition | Unit | Value |
| Density | g/cc | 0.7615 |
| Nitrogen | ppm w | 16 |
| n-Paraffins | W % | 4.4 |
| i-Paraffins | W % | 25.0 |
| Olefins | W % | 26.7 |
| Naphtenes | W % | 9.1 |
| Aromatics | W % | 33.0 |
| Oxygenates | W % | 1.8 |
| SIMDIST* (D2887) | | |
| 0 W % | ° C. | 13 |
| 5 W % | ° C. | 20 |
| 10 W % | ° C. | 25 |
| 30 W % | ° C. | 64 |
| 50 W % | ° C. | 101 |
| 70 W % | ° C. | 147 |
| 90 W % | ° C. | 194 |
| 95 W % | ° C. | 213 |
| 100 W % | ° C. | 247 |

* SimDist (D2887) is a Simulated Distillation System for ASTM D2887, designed to determine the boiling range distribution of petroleum product.

The Examples below describe processes for aromatic Alkylation and deolefinization of the FCC Naphtha Stream of Table 1. In the examples below, the operating conditions are the same, the only variable being the nature of the catalyst. Details of the reaction conditions, catalyst and results are shown in the examples below.

Example 2: Aromatic Alkylation and Deolefinization of FCC Naphtha Stream—Using Modified USY Zeolite Containing Catalyst with No Active Phase Metals A modified USY zeolitic containing catalyst in powder form without any active phase metals was used. The catalyst contains about 35 W % zeolite on alumina support. As seen in Table 2, the diesel yield increased by only 4 W % at the maximum catalyst to oil ratio.

TABLE 2

| Experiment# | Unit | RPHSA-4 |
|---|---|---|
| Temperature | ° C. | 90 |
| Pressure | bars | 1 |
| LHSV Equivalent | $h^{-1}$ | 3.80-37.77 |
| Catalyst | | Modified USY without metals |
| Catalyst form | | Powder |
| Results | | |
| Cut Point between Naphtha/Diesel | ° C. | 160 |
| Diesel yield in feedstock | W % | 22 |
| Diesel Yield in product Cat/Oil = 0.0066 | W % | 26 |
| Diesel Yield in product Cat/Oil = 0.013 | W % | 26 |
| Diesel Yield in product Cat/Oil = 0.026 | W % | 26 |
| Diesel Yield in product Cat/Oil = 0.039 | W % | 26 |
| Diesel Yield in product Cat/Oil = 0.053 | W % | 26 |
| Diesel Yield in product Cat/Oil = 0.066 | W % | 27 |

Example 3: Aromatic Alkylation and Deolefinization of FCC Naphtha Stream—Using Modified USY Zeolite Containing Catalyst with Active Phase Metals (Extrudate Form)

A modified USY zeolitic catalyst in extrudate form with active phase metals (Ni=4 W %, Mo=16 W %) was used in this example. The catalyst contains about 30 W % zeolite on alumina support. As seen in Table 3, the diesel yield of the product (RPHSA-5) increased by only 7 W % at the maximum catalyst to oil ratio.

TABLE 3

| Experiment# | Unit | RPHSA-5 |
|---|---|---|
| Temperature, ° C. | Unit | 90 |
| Pressure, bars | | 1 |
| LHSV Equivalent | $h^{-1}$ | 1.38-10.58 |
| Catalyst | | Modified USY with metals |
| Catalyst form | | Extrudate |
| Results | | |
| Cut Point between Naphtha/Diesel | ° C. | 160 |
| Diesel yield in feedstock | W % | 22 |
| Diesel Yield in product Cat/Oil = 0 | W % | 24 |
| Diesel Yield in product Cat/Oil = 0.022 | W % | 28 |
| Diesel Yield in product Cat/Oil = 0.043 | W % | 27 |
| Diesel Yield in product Cat/Oil = 0.087 | W % | 27 |
| Diesel Yield in product Cat/Oil = 0.131 | W % | 28 |
| Diesel Yield in product Cat/Oil = 0.175 | W % | 29 |

Example 4: Aromatic Alkylation and Deolefinization of FCC Naphtha Stream—Using Modified USY Zeolite Containing Catalyst with Active Phase Metals (Powder Form)

A modified USY zeolitic catalyst in powder form with active phase metals (Ni=4 W %, Mo=16 W %) was used in this example. The catalyst contains about 30 W % zeolite on alumina support. As seen in Table 4, the diesel yield of the product (RPHSA-6) increased by only 14 W % at the maximum catalyst to oil ratio.

TABLE 4

| Experiment# | Unit | RPHSA-6 |
|---|---|---|
| Temperature, ° C. | | 90 |
| Pressure, bars | | 1 |
| LHSV Equivalent | $h^{-1}$ | 1.08-10.58 |
| Catalyst | | Modified USY with metals |
| Catalyst form | | Powder |
| Results | | |
| Cut Point between Naphtha/Diesel | ° C. | 160 |
| Diesel yield in feedstock | W % | 22 |
| Diesel Yield in product Cat/Oil = 0.022 | W % | 36 |
| Diesel Yield in product Cat/Oil = 0.043 | W % | 35 |
| Diesel Yield in product Cat/Oil = 0.088 | W % | 35 |
| Diesel Yield in product Cat/Oil = 0.131 | W % | 35 |
| Diesel Yield in product Cat/Oil = 0.175 | W % | 35 |
| Diesel Yield in product Cat/Oil = 0.219 | W % | 36 |

Results

Figure 1B:
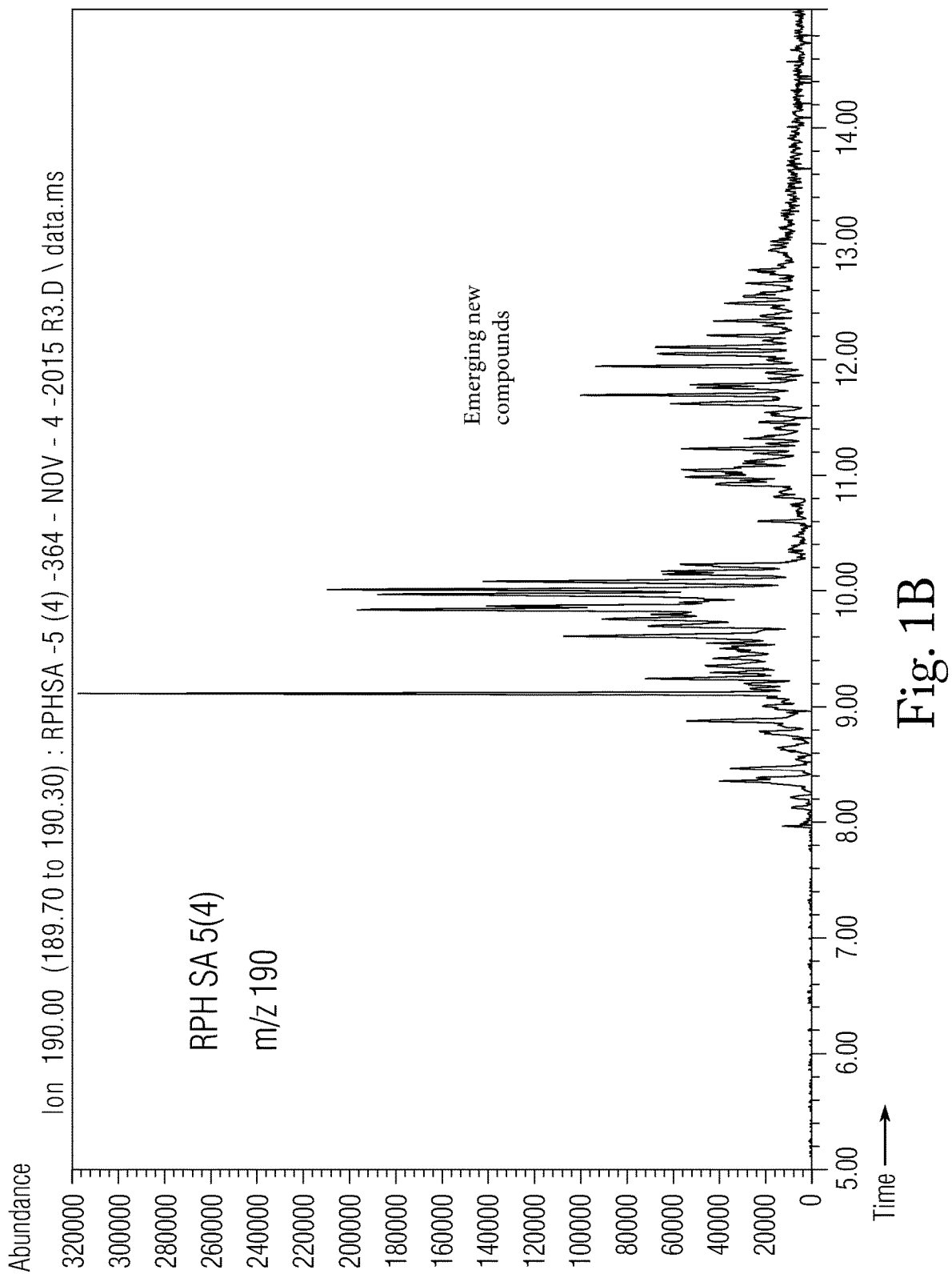

The feedstock (Example 1) and products of the reaction of Example 4 were analyzed by GC-MS to prove the aromatic formation. As seen in FIG. 1, newly formed compounds were observed in the GC-MS.

Figure 2A:
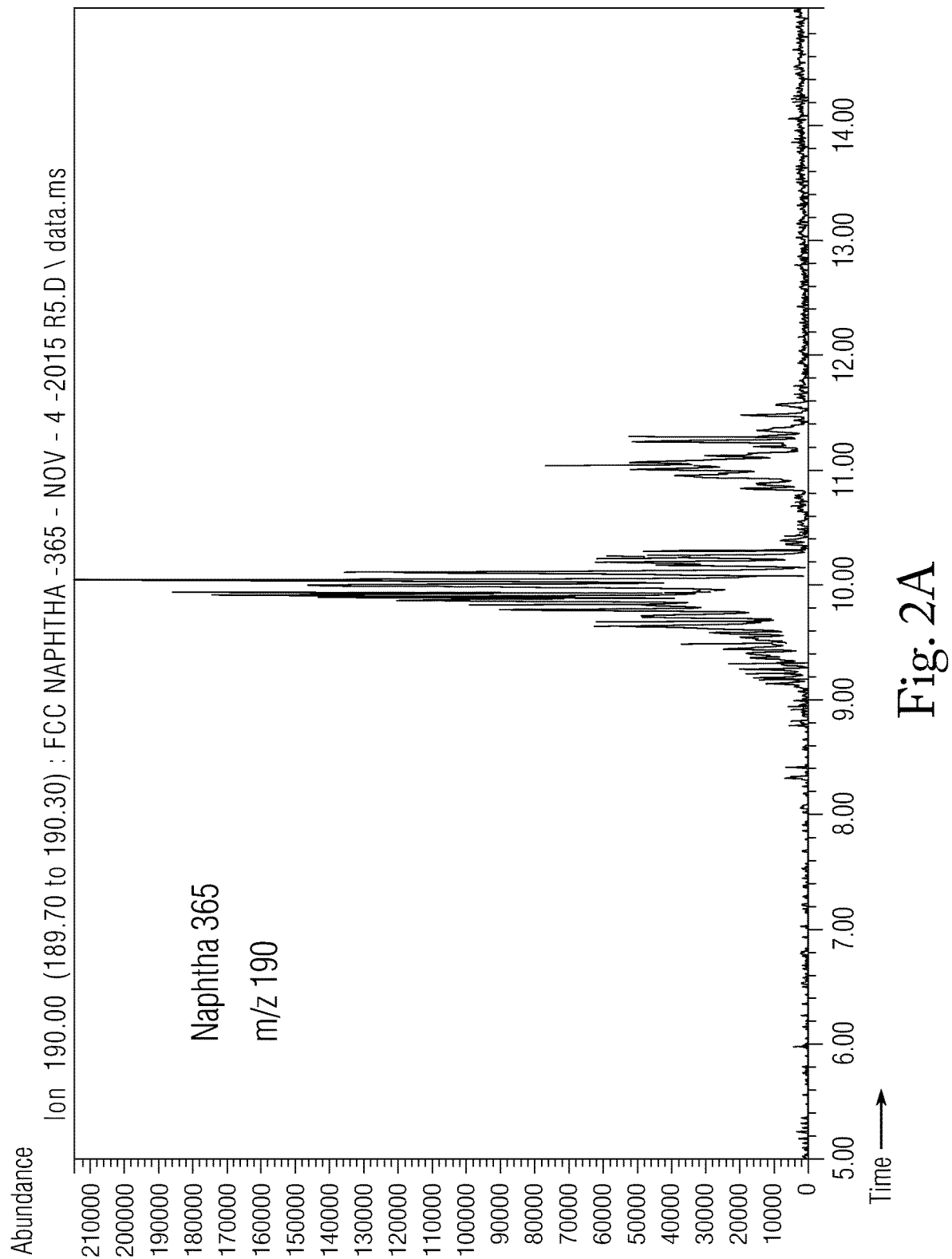
FIGS. 2A-2B depicts GC-MS comparisons of the m/z 190 ion of a FCC naphtha feed (FIG. 2A, Naphtha 365) and reaction product RPHSA-6 (FIG. 2B).
Figure 2B:
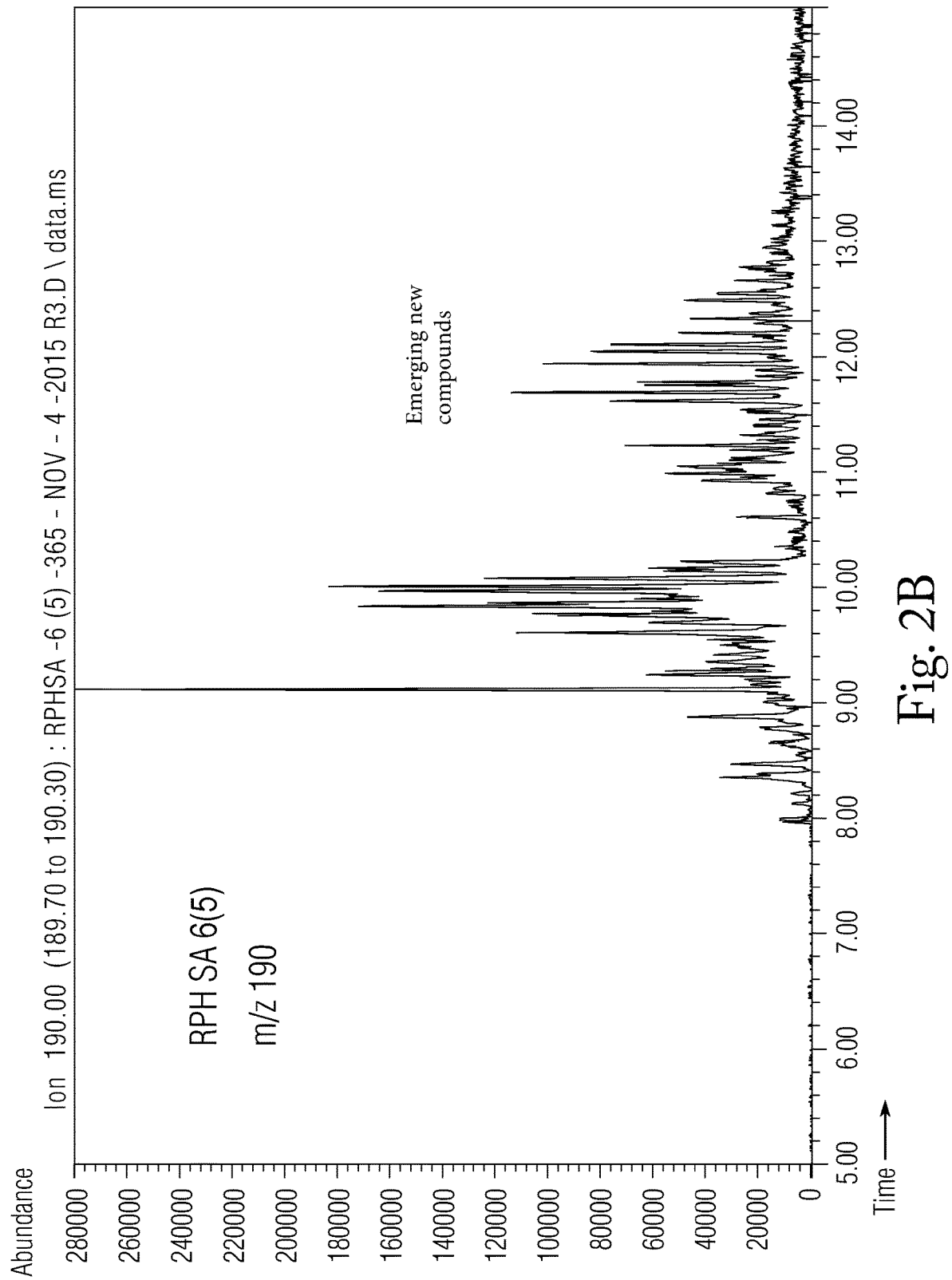

FIG. 1 depicts gas chromatography-mass spectrometry (GC-MS) comparisons of the m/z 190 ion between the initial FCC naphtha feed and the product RPHSA-5. FIG. 2 depicts gas chromatography-mass spectrometry (GC-MS) comparisons of the m/z 190 ion between the initial FCC naphtha feed and the product RPHSA-6. The m/z 190 ion was selected as a point of reference. The m/z 190 ion can be used to display essentially all C6 toluene compounds (i.e., C7 benzene compounds). As shown, there is a clear difference between the feed and the alkylated samples for each experiment (as shown by the area of focus—"emerging new compounds"). The highlighted peaks in the RPHSA-6 product show the emergence of new product species at increased residence times corresponding to the heavier products being formed. GC-MS analysis reveals that aromatic compounds are created and increase as a function of catalyst loading.

Figure 3:
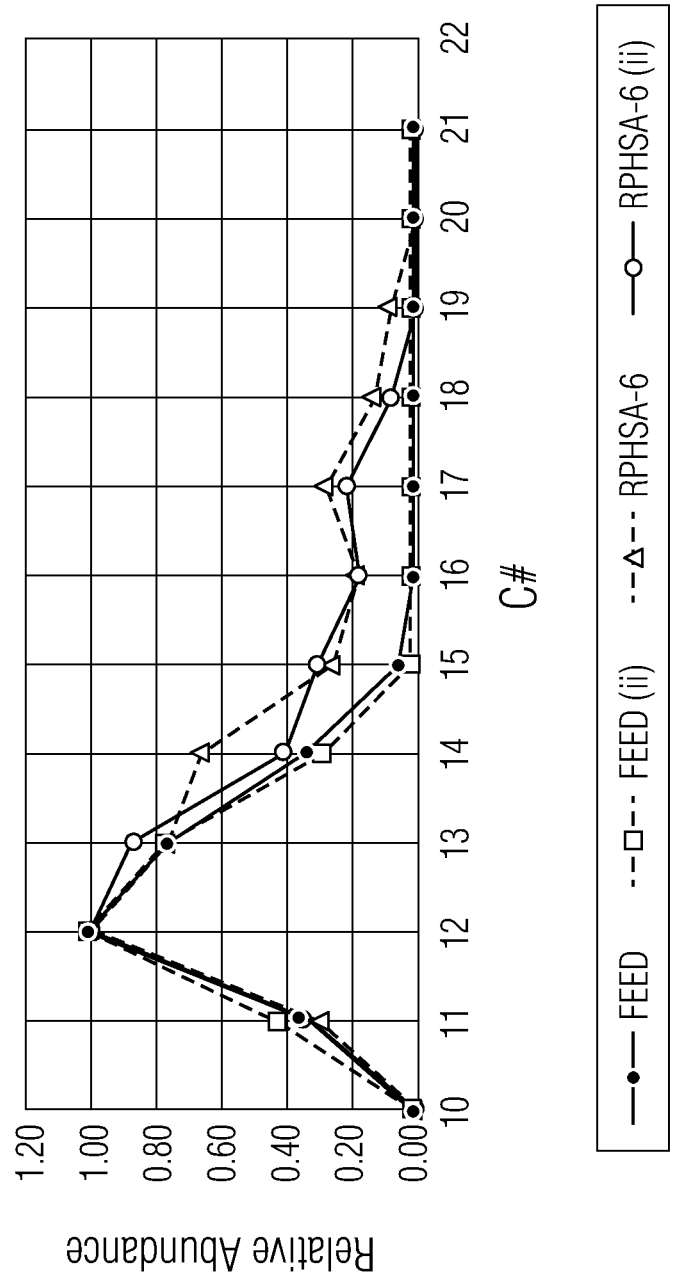
FIG. 3 Carbon number equivalent for RPHSA-6 and the initial FCC naphtha feed. Experiments were conducted in duplicates. Feed(i) (-○-); Feed(ii) (---■---); RPHSA-6(i) (---◆---); RPHSA-6 (ii) (-●-).

FIG. 3 depicts the carbon number equivalent for RPHSA-6 (5) and the initial feed (Table 1) (performed in duplicate). FT-MS analysis reveals that the FCC naphtha alkylation took place adding approximately 4-8 carbon atoms on average.

Figure 4:
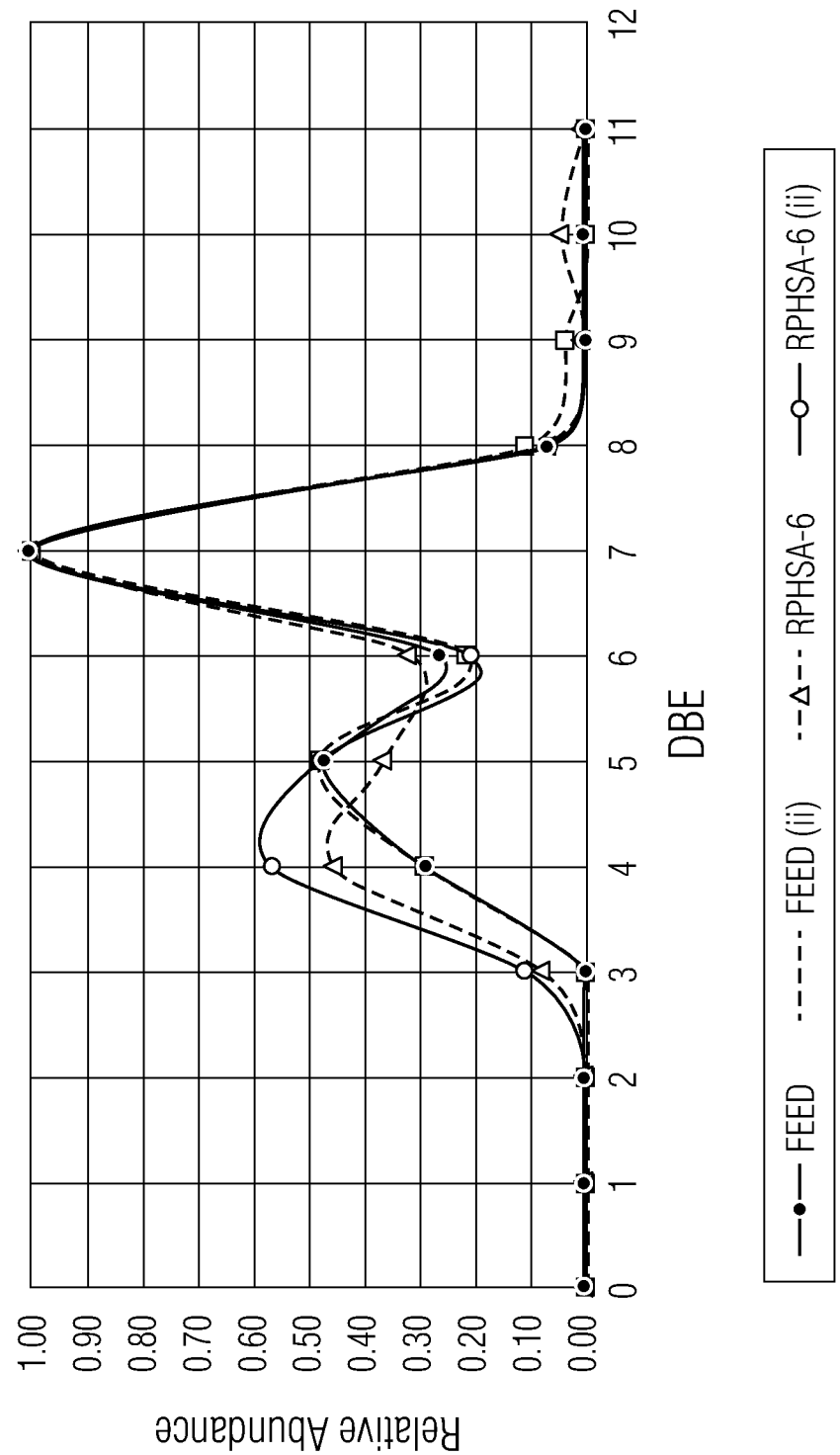
FIG. 4 Double bond equivalence of the product and the initial FCC naphtha feed. Feed(i) (-○-); Feed(ii) (---■---); RPHSA-6(i) (---◆---); RPHSA-6 (ii) (-●-).

FIG. 4 depicts the double bond equivalence of the product and the initial FCC naphtha feed (performed in duplicate). It is noteworthy that, although average carbon number of the mixture is increased, the double bond equivalence remains similar.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A process for deolefinization of a hydrocarbon feed containing aromatic compounds and olefins, the process comprising the step of contacting the hydrocarbon feed with a catalyst containing a framework-substituted ultra-stable Y (USY)-type zeolite in which a portion of aluminum atoms constituting a zeolite framework thereof is substituted with zirconium atoms and/or titanium and/or hafnium atoms, wherein the olefins alkylate the aromatic compounds in the hydrocarbon feed, thereby producing a deolefinated hydrocarbon product.

2. The process according to claim 1, wherein the framework-substituted USY-type zeolite in the catalyst comprises zirconium atoms and titanium atoms.

3. The process according to claim 1, wherein the framework-substituted USY-type zeolite in the catalyst comprises from about 0.1 to about 5% by mass zirconium and/or titanium and/or hafnium atoms, each calculated as the oxide basis.

4. The process according to claim 1, wherein the framework-substituted USY-type zeolite in the catalyst further includes a support comprising inorganic oxides selected from the group consisting of alumina, silica-alumina and combinations thereof.

5. The process according to claim 1, wherein the hydrocarbon feed comprises an aromatic rich hydrocarbon oil having a boiling point range of about 15° C. to about 500° C.

6. The process according to claim 1, wherein the contacting is operated at reaction temperature range of about 50° C. to about 250° C., a pressure of about 1 to about 30 bars and a liquid hourly space velocity (LHSV) of about 0.5 to about 50 $h^{-1}$.

7. The process according to claim 1, wherein the deolefinated product contains less than about 500 ppm sulfur.

8. The process according to claim 1, wherein the deolefinated hydrocarbon product containing less than about 100 ppm nitrogen.

9. The process according to claim 1, wherein the hydrocarbon feed contains greater than about 1 wt % olefins.

10. The process according to claim 1, wherein the deolefinated hydrocarbon product contains less than about 10 wt % olefins.

11. The process according to claim 1, wherein the hydrocarbon feed is deolefinated at least about 95 wt %.

12. The process according to claim 1, wherein the deolefinated hydrocarbon product has bromine index less than about 60,000.

13. The process according to claim 1, wherein the aromatic compounds in the hydrocarbon feed contains benzene and alkylated benzenes.

14. The process according to claim 13, wherein the aromatic compounds in the hydrocarbon feed comprise C6 to C10 aromatic compounds.

15. The process according to claim 1, wherein the deolefinated hydrocarbon product comprises less olefin hydrocarbons and more alkylated aromatic compounds as compared with the hydrocarbon feed.

16. The process according to claim 1, wherein the hydrocarbon feed is fluid catalytic cracking (FCC) naphtha, coking naphtha or other naphtha coming from the cracking units in which no hydrogen is used.

17. The process according to claim 1, wherein the catalyst further includes an active metal selected from the group consisting of IUPAC Group 7 to 11 metal of the Periodic Table.

18. The process according to claim 1, wherein the deolefinated product contains less than about 10 ppm sulfur.

19. The process according to claim 1, wherein the deolefinated product contains less than about 0.5 ppm sulfur.

20. The process according to claim 1, wherein the deolefinated hydrocarbon product containing less than about 10 ppm nitrogen.

21. The process according to claim 1, wherein the deolefinated hydrocarbon product containing less than about 0.5 ppm nitrogen.

22. The process according to claim 1, wherein the deolefinated hydrocarbon product contains less than about 1 wt % olefins.

23. The process according to claim 1, wherein the deolefinated hydrocarbon product contains less than about 0.5 wt % olefins.

24. The process according to claim 1, wherein the hydrocarbon feed is deolefinated at least about 99 wt %.

25. The process according to claim 1, wherein the hydrocarbon feed is deolefinated at least about 99.99 wt %.

26. The process according to claim 1, wherein the deolefinated hydrocarbon product has bromine index less than about 10,000.

27. The process according to claim 1, wherein the deolefinated hydrocarbon product has bromine index less than about 1,000.

28. A process for alkylating aromatic compounds in a hydrocarbon feed containing aromatic compounds and olefins, the process comprising the step of contacting the hydrocarbon feed with a catalyst containing framework-substituted ultra-stable Y (USY)-type zeolite in which a portion of aluminum atoms constituting a zeolite framework thereof is substituted with zirconium atoms and/or titanium and/or hafnium atoms, wherein the olefins alkylate the aromatic compounds in the hydrocarbon feed, thereby producing alkylated aromatic compounds.

* * * * *